United States Patent
Blaha et al.

(10) Patent No.: US 10,551,304 B2
(45) Date of Patent: Feb. 4, 2020

(54) EXPLOSIVES DETECTOR AND METHOD FOR DETECTING EXPLOSIVES

(71) Applicant: RS DYNAMICS GMBH, Zug (CH)

(72) Inventors: Jiri Blaha, Oberägeri (CH); Jan Dupač, Prague (CZ); Michal Zástěra, Prague (CZ); Roman Mázl, Prague (CZ)

(73) Assignee: RS DYNAMICS GMBH, Zug (CH)

( * ) Notice: Subject to any disclaimer, the term of this patent is extended or adjusted under 35 U.S.C. 154(b) by 0 days.

(21) Appl. No.: 16/024,184

(22) Filed: Jun. 29, 2018

(65) Prior Publication Data
US 2019/0017928 A1   Jan. 17, 2019

Related U.S. Application Data (63) Continuation-in-part of application No. 14/425,516, filed as application No. PCT/IB2012/001693 on Sep. 3, 2012, now abandoned.

(51) Int. Cl.
*G01N 21/3504* (2014.01)
*G01N 21/84* (2006.01)
(Continued)

(52) U.S. Cl.
CPC ..... *G01N 21/3504* (2013.01); *G01N 21/8483* (2013.01); *G01N 33/0057* (2013.01); *G01N 33/227* (2013.01); *G01N 21/76* (2013.01)

(58) Field of Classification Search
CPC ........... G01N 21/3504; G01N 21/8483; G01N 33/0057; G01N 33/227; G01N 21/76
See application file for complete search history.

(56) References Cited

U.S. PATENT DOCUMENTS

| 5,092,155 A * | 3/1992 | Rounbehler | G01N 1/02 436/156 |
| 5,123,274 A * | 6/1992 | Carroll | G01N 1/02 436/156 |

(Continued)

FOREIGN PATENT DOCUMENTS

WO   2007002037 A2   1/2007

OTHER PUBLICATIONS

International Search Report of corresponding PCT/IB2012/001693, dated Dec. 11, 2012.

*Primary Examiner* — Christine S. Kim
(74) *Attorney, Agent, or Firm* — Maginot, Moore & Beck LLP (57) ABSTRACT

An explosives detector includes an infrared sampler having a flat infrared radiation source suitable for release of a solid explosive sample from a surface of a scanned subject using a wavelength of an infrared radiation, and a thermal decomposition unit having a silica glass tube with a silica glass tube gas inlet located in the flat infrared radiation source, wherein the silica glass tube is equipped with a heating element, the thermal decomposition unit being suitable for decomposing the solid explosive sample into a plurality of explosive molecular fragments. The explosives detector further includes a detector cartridge, having a cartridge body with a detection liquid inside, a molecular detection membrane fully submerged under a level of the detection liquid, and a sensing cap, where each explosive molecular fragment is detected by said detector cartridge and a single photon optical detection unit in communication with detector cartridge to provide a data stream indicative of explosive molecular fragment's presence in the solid explosive sample.

7 Claims, 6 Drawing Sheets

(51) Int. Cl.
  *G01N 33/22*  (2006.01)
  *G01N 33/00*  (2006.01)
  *G01N 21/78*  (2006.01)
  *G01N 21/76*  (2006.01)

(56) References Cited

U.S. PATENT DOCUMENTS

| | | | |
|---|---|---|---|
| 5,912,466 A * | 6/1999 | Funsten | G01N 1/2208 |
| | | | 250/372 |
| 6,946,300 B2 * | 9/2005 | Nguyen | G01N 1/24 |
| | | | 356/36 |
| 6,984,524 B2 | 1/2006 | Nguyen | |
| 9,005,524 B2 | 4/2015 | Dean | |
| 2003/0085348 A1 | 5/2003 | Megerle | |
| 2004/0169845 A1 * | 9/2004 | Nguyen | G01N 1/24 |
| | | | 356/36 |
| 2007/0086925 A1 * | 4/2007 | O'Donnell | G01N 1/2214 |
| | | | 422/82.05 |
| 2009/0113982 A1 * | 5/2009 | Hodyss | G01N 30/74 |
| | | | 73/1.06 |
| 2009/0252650 A1 | 10/2009 | Lakshmanan | |
| 2010/0240140 A1 | 9/2010 | Fine | |
| 2011/0132108 A1 * | 6/2011 | Novosselov | G01N 1/2202 |
| | | | 73/863.22 |
| 2011/0203931 A1 * | 8/2011 | Novosselov | G01N 1/2202 |
| | | | 204/600 |
| 2011/0271738 A1 * | 11/2011 | McGill | G01N 21/64 |
| | | | 73/23.41 |
| 2014/0362226 A1 | 12/2014 | Xu | |
| 2018/0348184 A1 * | 12/2018 | Nguyen | G01N 33/0037 |

* cited by examiner

Fig. 6

EXPLOSIVES DETECTOR AND METHOD FOR DETECTING EXPLOSIVES

CROSS REFERENCE TO RELATED APPLICATIONS

The present application is a continuation-in-part of U.S. patent application Ser. No. 14/425,516, filed Nov. 12, 2015, which is a 371 of International Patent Application No. PCT/IB2012/001693, filed Sep. 3, 2012. The disclosure of the above applications are hereby incorporated by reference in their entirety.

FIELD OF THE INVENTION

This invention relates to an explosives detector and to a method for the detecting explosives.

BACKGROUND OF THE INVENTION

Current technologies used for detection of explosive traces are based on direct air sampling of explosive vapor surrounding explosive contraband or are based on a particulate sampling technique. The direct air sampling technique is effective only for sufficiently volatile explosive components, while the explosive components mostly used for creation of so-called plastic explosives feature very low or zero volatility at ambient temperature.

There is a world-wide demand for reliable contact-less explosive detection technologies, being capable to sample and detect all kinds of explosive compounds, mainly widely used non-volatile or home-made explosive agents.

Most of the current detection technologies use an IMS (Ion Mobility Spectrometry) detection principle, or other technologies focused for direct identification of the sample. Unfortunately, those detection principles are very sensitive to cross-talk by various disturbing chemicals and saturation due to very limited dynamic range. Both above mentioned limitations create potentially a high false alarm rate and cause moreover a number of serious problems with after-exposure cleaning of the system.

The current portable system works mostly in the cycle "sampling—pre-concentration—analysis". This operation cycle requires an operator to sample just from one spot, in the good belief this spot contains the found traces. There is no indication about the properly selected spot during the sampling interval, so it frequently happens to sample from the improper spot or location, while losing valid operational time.

Most of the current systems utilizing various detection technologies, namely IMS, are quite complicated, climatic condition-sensitive instruments, and are not very suitable for heavy-duty field and/or military application. Also, they require an advanced level of operator's qualification and demanding training of the operator.

Most of today's operators need to scan the controlled subjects (parcels, baggage, people) only in vapor mode, which under standard sampling conditions is typically not successful, namely in the case of plastic explosives (and all other non-volatile explosives). Such substances create no vapors at normal ambient temperature and hence no vapor traces can be sampled/detected in standard vapor mode.

Systems and methods for reliable detection of various explosives are urgently needed and are now at the forefront of many research efforts. The wanted detection system should be reliable, sensitive, of a small size for handheld use, operating preferably only in vapor mode, resistant against cross-talking chemicals to avoid false alarms and simple for operation, so as not to require extensive training or special education of an operator. Under the standard environmental conditions, the detection of explosives is a complicated and complex task, especially considering the detection of all variants of non-volatile types of explosives and disturbing factors of the variety of environmental condition (humidity, dust, temperature). Moreover, interference from various chemicals, human sweat, various solvents etc. lead to false alarms, which are obviously difficult to distinguish from actual positive detection.

The wide variety of techniques used to sample explosives include the manual swiping of the scanned subject in a so-called particulate mode or the sampling of air surrounding the scanned subject at ambient temperature and consequent pre-concentration in a good belief to collect most of the traces in the vicinity of the scanned subject. The manual swiping is not very popular or sometimes difficult to apply and the air sampling requires huge amount of air to be sampled and pre-concentrated to collect enough volume of traces to satisfy the system detection limit.

The variety of techniques used to detect/analyze explosives, based on ion mobility spectrometry, infrared spectroscopy, micro-wave spectroscopy, Raman or fluorescence spectrometry, bring good detection results. However all those principles feature low dynamic range and are sensitive to cross-talk caused by interfering chemicals or overload and suffer from difficult cleaning if exposed by huge sampled concentration. Portable detection systems built on above principles are usually complicated, big, heavy and not operationally robust enough to work reliably in the demanding field conditions, which are characterized by changing humidity, temperature, dust and rough handling by the operator. A high level of operator training and adequate operator education is obviously necessary for successful detection using above technologies, which limits the range of people usable to execute the detection operation.

SUMMARY OF THE INVENTION

The current invention relates to a system and method for a fast, sensitive and continuous vapor-mode detection of explosives.

The present disclosure further relates to the technical design and construction of an explosive detector using infrared continuous sampling technology together with a thermal decomposition detection unit integrated in one body with an infrared sampler according to the invention.

The explosive detector according to this invention is built compact in a pocket size with a light-weight body, especially shaped for the whole-day wearing on a law enforcement officer's belt.

In another embodiment, the new explosive detector works in direct infrared continuous vapor mode with instant reading, not requiring sampling, pre-concentration and an analyzing period.

In yet another embodiment, a new flat infrared source transmits the infrared radiation directly to the surface to be scanned for ideal release of all volatile and also non-volatile explosive traces.

In yet another embodiment, the infrared sampler is integrated into one body with a thermal decomposition unit for a fast detection, in order to minimize the losses of the scanned traces volume, and to minimize the battery energy consumption.

In yet another embodiment, the thermal decomposition unit, which is directly integrated in one body with the infrared radiation source, is composed of a silica-glass tube with an on-surface integrated non-linear heating element to achieve a minimal temperature gradient along the length of the thermal decomposition tube and to achieve a precise regulation of the operating temperature.

In yet another embodiment, the thermal decomposition unit is housed in a special thermal insulating cylinder for optimal shape of the temperature gradient and for minimizing the temperature loses.

In yet another embodiment, the new detection cartridge with a molecular membrane submerged in a detection liquid is used for a reliable and long-term stable detection of photons as a response to the decomposed explosive molecules coming into reaction with a detection liquid.

In yet another embodiment, the shape of the detection cartridge is especially designed to permit the widest possible range of 3-D working angles of the cartridge, in order to achieve the detection membrane to be submerged in the detection liquid level within the widest operational angles.xxx In yet another embodiment, the gas output of the thermal decomposition unit is connected with the detection cartridge using especially designed needle line-up, enabling fast and reliable connection and/or change of the detector cartridge.

In yet another embodiment, the new detection cartridge consists of the main cartridge body housing the special detection liquid, the sunk detection polymer membrane and the sensing cap and creating the detection annular chamber for the convolute circulation of the detected gas along of the dry membrane surface together with a proper connection to the connecting needles, wherein the glossy optical window for detecting photons is created at the wet side of the membrane to pass through the layer of the detection liquid and through this window the optical single photon detection unit is created.

In yet another embodiment, the construction shape of the detection cartridge is designed for the tightest possible displacement and optical connection to the single-photon optical detection unit.

In yet another embodiment, the construction shape of the detection cartridge is designed for the one-movement easy cartridge deployment to the connection needles line-up and easy replacement of the used cartridge.

In yet another embodiment, the detection cartridge is equipped with special pulling handle for easy manipulation and removal from its slot.

In yet another embodiment, the detection cartridge is equipped with a soft plastic optical shield to avoid penetration of even the weakest interfering light into the cartridge.

In yet another embodiment, the detection cartridge is inserted into the rectangular slot, created inside the one-body instrument frame, housing also a newly developed single photon optical detection unit.

In yet another embodiment, the one-body instrument frame contains two slots, one for the detection cartridge and the other one for the single-photon optical detection unit to secure minimal distance between the photo sensing element of the single-photon optical detection unit and the detection cartridge optical window.

In yet another embodiment, the one-body instrument frame creates the holding slot with the silent-block vibration insulation support for the vibration pump installation.

In yet another embodiment, the one-body instrument frame creates the mounting points for a 3-D assembly of a 3-D Flex PC board, comprising all the system electronics, the communication connectors and the battery connectors.

In yet another embodiment, the one-body instrument frame contains the mounting points for connecting the front analytical part containing the infrared continuous sampler and the thermal decomposition detection unit.

In yet another embodiment, the one-body instrument frame contains one system mounting point for fixing the whole instrument formation into the rectangular-tube-shaped explosive detector case.

In another embodiment, the explosive detector case is made of carbon-fiber plastic to achieve sufficient durability and robustness.

In still another embodiment, the newly designed single-photon detection unit according to at least some embodiments of this invention is used to achieve a high level of system sensitivity.

In still another embodiment, the new system is equipped with a built-in Wi-Fi module, located on the common 3-D Flex PC board for wireless remote control and data transfer.

In still yet another embodiment, the multi-processor built-in computer and the operational software are designed to control all the operations and to achieve an easy user-friendly operation.

In still yet another embodiment, only one button is used to operate all the system functions due to intelligent, user-friendly operational software.

In still yet another embodiment, the full graphic color screen is used to provide transparent, user-friendly communication and detection results to the operator.

In still yet another embodiment, the software is also useable for easy wireless remote control for a robotic application.

In still yet another embodiment, the software is also useable for remote internet factory checking and first-level factory repair of the system.

In yet another embodiment, four Lithium-Polymer battery cells are used as the main system rechargeable battery, housed in a robust carbon-fibers battery case following the shape of the whole unit.

The present disclosure further relates to the method for detecting explosives comprising: infrared release of a solid explosive sample from a surface of a scanned subject using a dedicated wavelength of an infrared radiation, thermal decomposition of the obtained solid explosive sample, converting the decomposed molecule's concentration to an optical signal, analyzing a shape of time peak of the optical signal to distinguish interfering components from a signal of interest and to remove wide spectrum noise and signal fluctuations of various origin and analyzing the data obtained from above signal processing, displaying the data in numerical and/or graphical form on a color graphic screen and storing the data to a system flash disk.

The main advantage of at least some embodiments of this invention is the reliable detection of explosives, using infrared sampling technique built into a pocket-sized, explosive detector. The explosive detector according to the invention is equipped with various ways to communicate with surroundings. For manufacturer set up, calibration and software update, a standard RS232 port is provided, using the advantages of simplicity and reliability of the communication protocol. A customer can use either a standard USB 2.0 port, with standard micro-USB connector and cable to connect the unit to a PC, or a built-in WIFI module for a convenient remote data transfer and/or full remote-control operation and internet remote communication.

Special remote-control software for PC and also for mobile Android platform, using the wire-less WIFI connection, have been developed for convenient application of the explosive detector according to the invention and for outdoor/indoor field robotic application according to the invention.

The test results prove, that the cost effective, sensitive, simple, and furthermore portable and fast explosives detector has been created for quantitative detection of explosive traces in the presence of other organic material by combining the infrared sampling with fast and sensitive thermal decomposition and an optical detection/analytical unit. The developed system according to at least some embodiments of the current invention, is technically simple and provides clear data of the presence and concentration of the explosive materials not disturbed by presence of the strong concentration of cross-talking organic chemical components.

BRIEF DESCRIPTION OF THE DRAWINGS

These and other features and advantages of the present invention will be better understood by reference to the following detailed description when considered in conjunction with the accompanying drawing wherein.

DETAILED DESCRIPTION OF THE INVENTION EMBODIMENTS

Unless defined otherwise, all the technical and scientific terms used herein have the same meaning as commonly understood to one of ordinary skills in the art to which this invention belongs.

The current invention addresses the technical solution and operating method of an explosives detector according to the invention, comprising an infrared sampler 1 operated in continuous mode, a thermal decomposition unit 2 and a single photon optical detection unit 3, followed by a control unit 4 with an implemented data acquisition, a communication unit 17 triggering an alarm. The explosives detector is capable of instant sampling and detection of even non-volatile explosives in real-time instant vapor mode. The whole detection system, including all the sampling, detection and analytical components is designed with the aim to achieve the sub-miniature construction and low-cost high-volume serial production to create an affordable and simple to operate explosive detector for everyday use of an operator with no need of special qualification and/or training.

Sampling System

Figure 1:
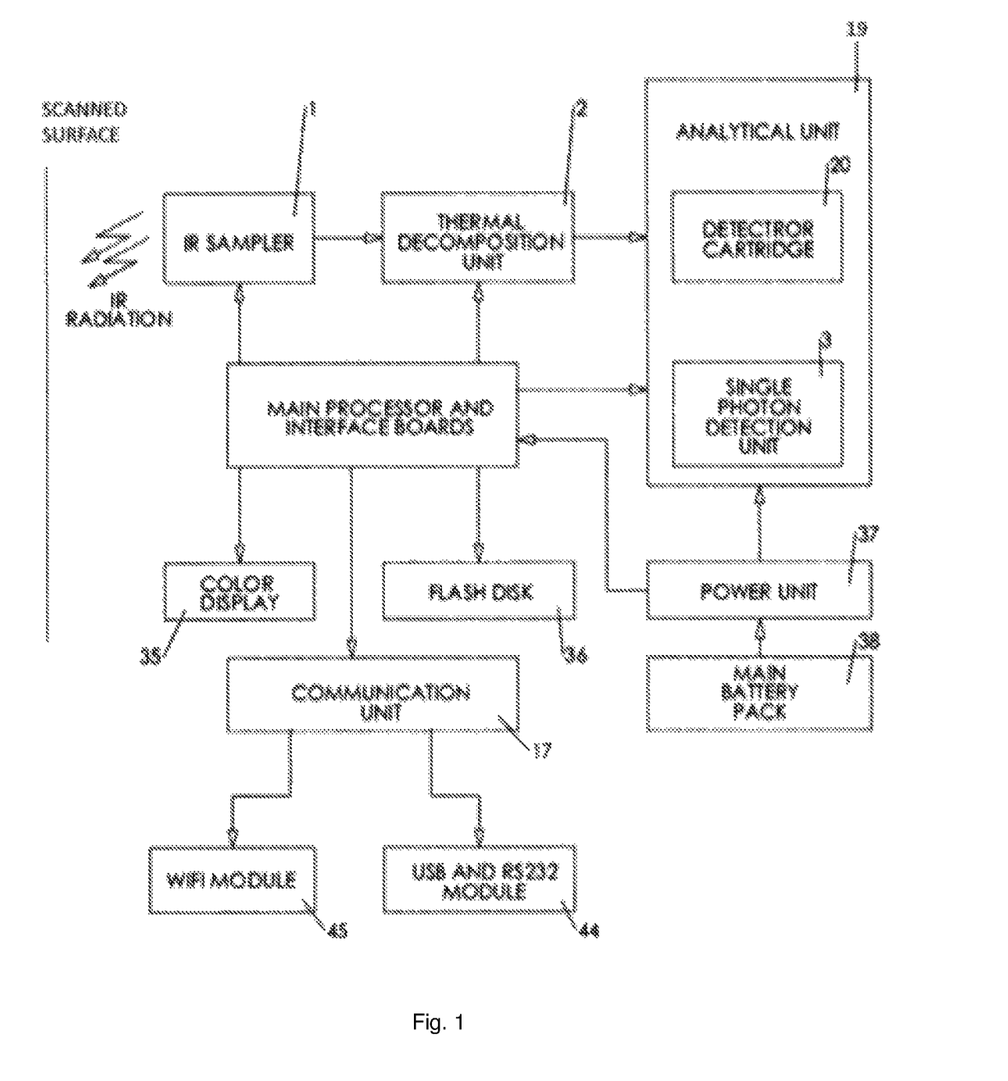
FIG. 1 shows a block diagram of an explosive detector according to the invention and particularly the detection system with infrared sampler, thermal decomposition unit, analytical unit, main processor and interface units with consequent control and data acquisition parts and power control and supply unit.

Turning to the sampling system, the new explosives detector uses infrared radiation energy of a selected wavelength to semi-selectively address explosive material molecules for their preferential release from solid to vapor phase (FIG. 1).

The sampling system of the explosive detector comprises a flat infrared radiation source 5 (FIG. 2, 5), emitting the generated infrared radiation energy homogeneously from its flat surface to the scanned surface.

Behind the flat infrared radiation source in direction to the interior of the explosive detector a helix-shaped radiation element 6 (FIG. 5) is arranged, providing a planar homogeneity of the radiated infrared energy.

The flat infrared radiation source 5 is covered with two-layers black thin-film daze shield 7 (FIG. 2) to allow mostly infrared radiation to pass through the shield and furthermore, to protect the flat infrared radiation source 5 against mechanical damage.

The thin-film black daze shield 7, respectively the flat infrared radiation source 5 is surrounded with a cone-shaped hood 8 (FIG. 5) for shielding the sampling process against the ambient blowing wind and the thin-film black daze shield 7 has a central circular aperture 9 (FIG. 5) of a silica glass tube gas input 10 to the thermal decomposition unit 2 for an explosive sample.

Figure 2:
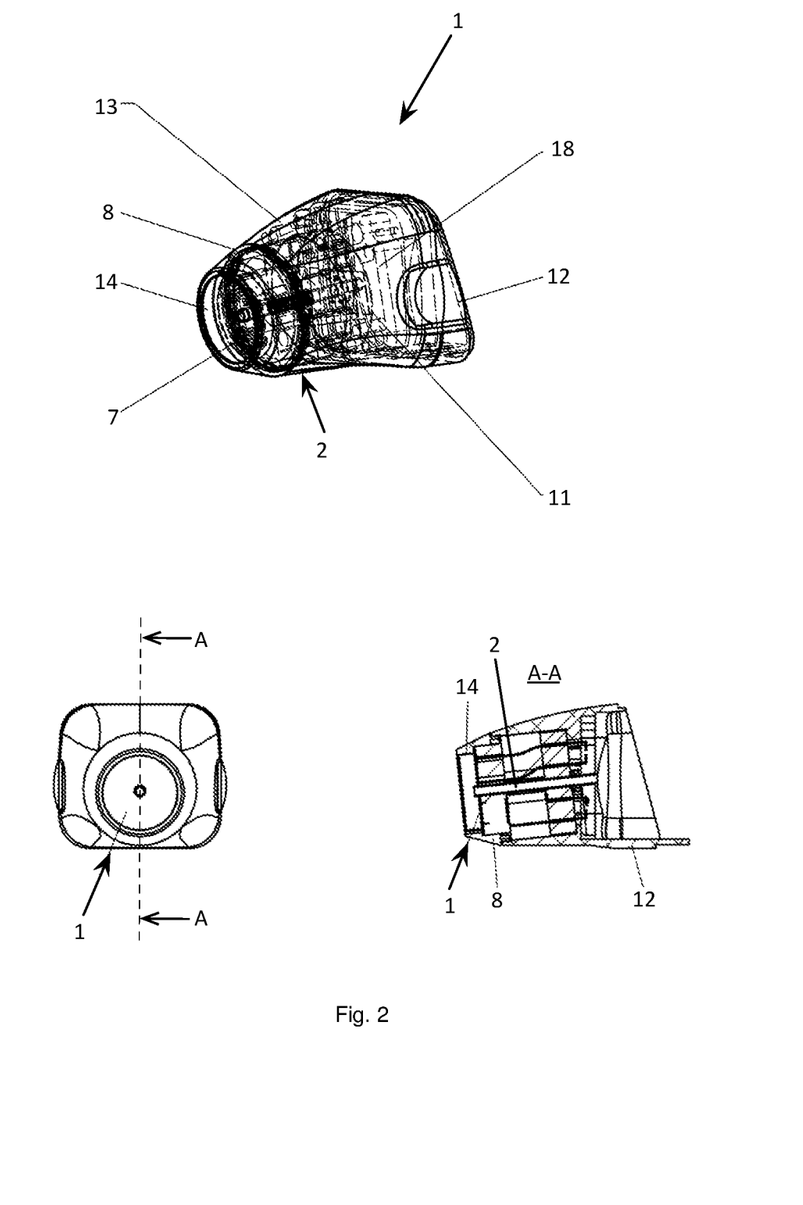
FIG. 2 shows the structure of an infrared sampler and a thermal decomposition unit of the explosive detector, together with a control electronics creating thus one building block of the explosive detector, wherein the upper fpart of FIG. 2 is the axonometrical view of the infrared sampler with the termal decomposition unit together with control electronics, all in one formation; wherein the lower part of FIG. 2 is the front view of the infrared sampler on the left side and a cross-section A-A of the whole formation is shown on the lower right side.

The flat infrared radiation source 5 with its black thin-film daze shield 7 is arranged in a temperature insulation cylinder 11 with a central cylindrical room for the seating of the thermal decomposition unit 2. (FIG. 2).

The explosive detector is housed in a robust, molded aluminum/magnesium body 12 (FIG. 2) for achieving operational robustness and good temperature dissipation.

The molded aluminum/magnesium body 12 is covered with polyurethane plastic skin 13 (FIG. 2) to avoid burning the operator's fingers and to absorb possible mechanical impact when the explosive detector would be dropped down to a hard surface.

The cone-shaped hood 8 (FIG. 2, 5) is made from chemically inert and temperature resistant material that is called "PEEK".

Analytical and Detection System

Figure 5:
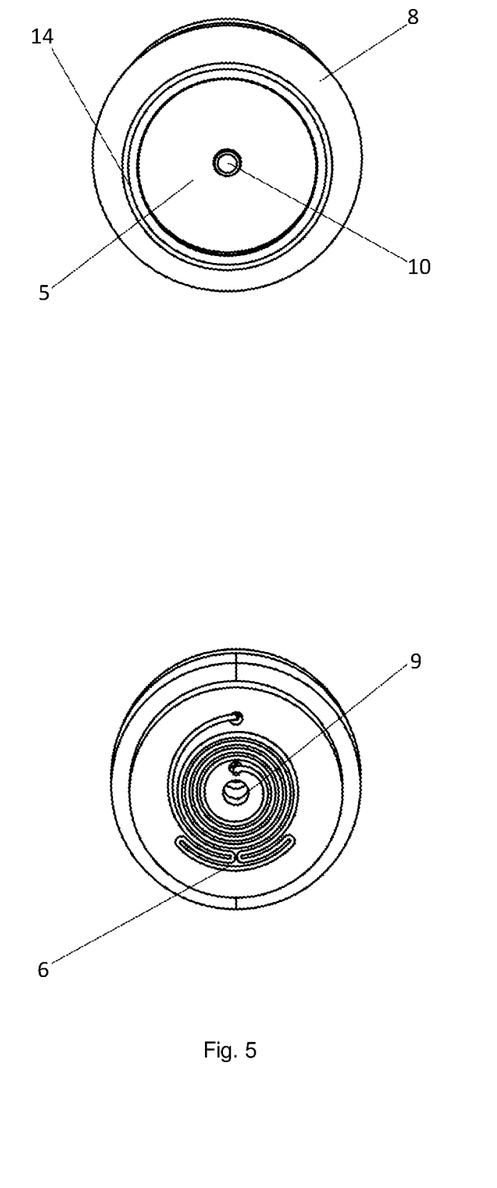
FIG. 5 shows a flat infrared radiation source and a helix-shaped radiation element with planar shape providing a planar homogeneuous radiation of infrared energy. In the upper part of FIG. 5 there is shown the front view of the flat infrared radiation source, and in lower part of FIG. 5, the helix-shaped radiation element is shown, which helix-shaped radiation element is arranged behind the flat infrared radiation source in the explosive detector according to the invention.
Figure 6:
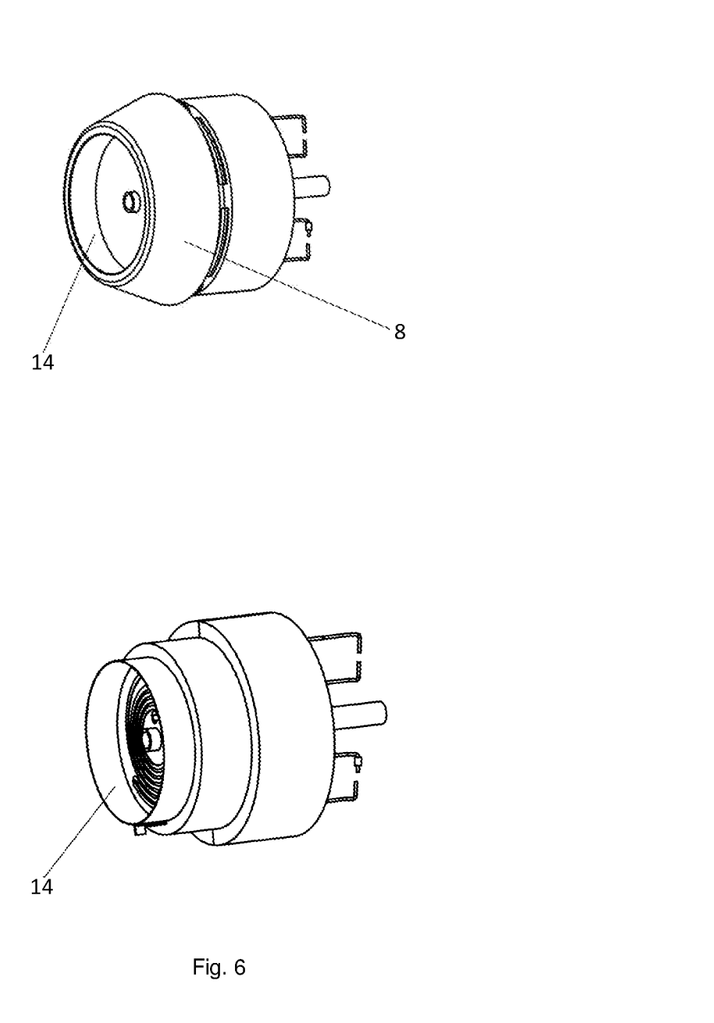
FIG. 6 shows in its upper part a cylindrical infrared sampler mirror laterally surrounding the flat infrared radiation source according to FIG. 5 and protected by a cone-shaped hood, and in the lower part of FIG. 6 the cylindrical infrared sampler mirror and the helix-shaped radiation element are shown with the cone-shaped hood and the flat infrared radiation source removed.

As shown in the block diagram provided in FIG. 1 in combined view with FIG. 2, once the traces of explosive samples from the scanned surface are released and converted to the vapor phase using the infrared radiation energy, the obtained explosive gas sample is directly sucked by an integrated vacuum pump 15 (housed in a neoprene pump support 16), into the thermal decomposition unit 2 (FIG. 2), having a gas input 10 located directly in the center of the flat infrared radiation source 5 (FIG. 2, 5). In this configuration, all the parts operate at the accurate temperature to avoid any condensation of the explosive sample, and features no losses of the explosive sample, due to installation of the detection/ analytical equipment just behind the flat infrared radiation source 5 (FIG. 2) and the fact that the operational temperature is kept constant during the operational time.

The thermal decomposition unit 2 comprises a silica glass tube with processed inner surface and a non-linear heating element located on the outer surface of the silica-glass tube, in the middle of the length of the silica glass tube.

The non-linear heating element is made of a heating wire, wound in non-linear way along the axis of the silica-glass tube, compensating thus for temperature drops given by location of the silica glass tube inside a temperature insulating cylinder 11, to achieve gradient-less distribution of the operating temperature along the silica glass tube.

The non-linear heating element is energized using a pulse width modulation mode for precise regulation of the temperature in the thermal decomposition unit 2 (FIG. 2).

The non-linear heating element is in addition used as a temperature sensing element during power pauses of a pulse width modulation cycle. This arrangement provides the closest temperature sensing of the silica glass tube, providing thus the most precise temperature measurement and regulation of the inner tube surface temperature for the most accurate operation of the thermal decomposition unit 2 provided by an integrated control electronic board 18.

The non-linear heating element is fixed in its non-linear displacement and operating position along the silica glass tube by a special high-temperature resistant cement.

Figure 3:
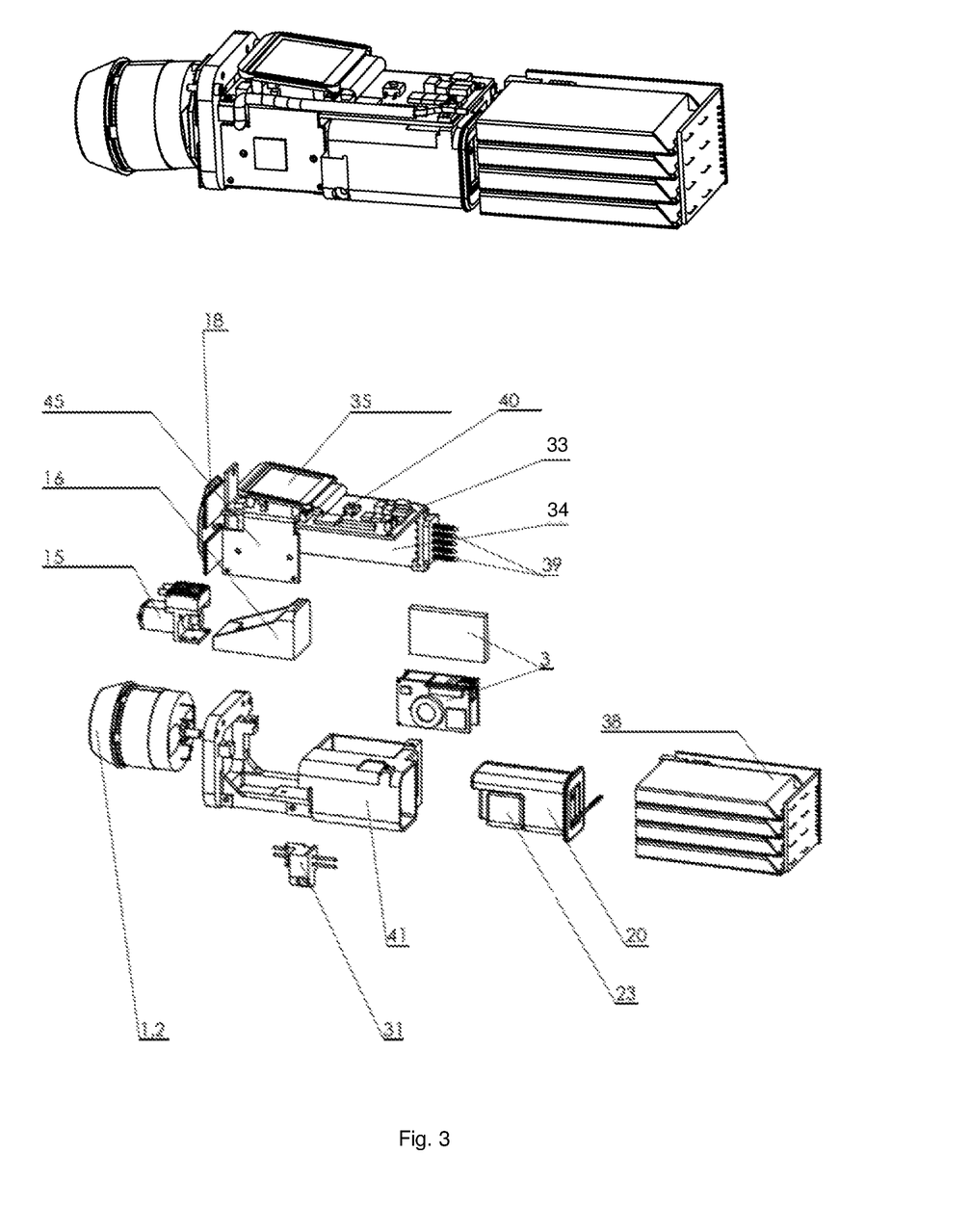
FIG. 3 shows an exploded drawing of further operational units of the explosive detector according to the invention.
Figure 4:
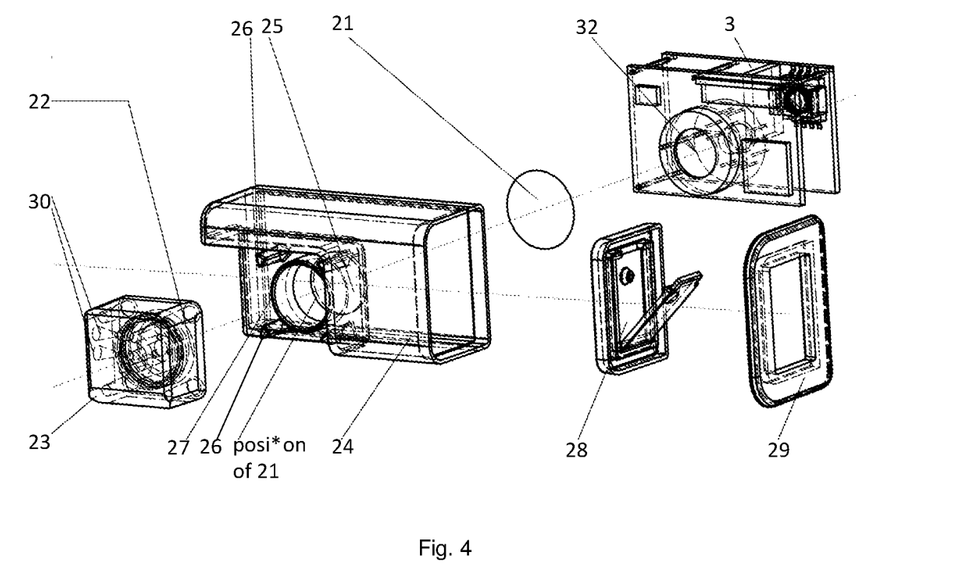
FIG. 4 shows a detector cartridge together with a single photon optical detection unit in an exploded drawing view.

The explosive gas sample is further transferred into an analytical unit 19, comprising a detector cartridge 20 (FIG. 1, 4) with a reaction annular chamber 22 (FIG. 4) created inside a sensing cap 23 (FIG. 3, 4) followed by an in-detection-liquid sunk (submerged) molecular membrane 21 (FIG. 4), and an optical single photon detection unit 3 (FIG. 4).

The detector cartridge 20 (FIG. 4) consists of a main cartridge body 24, made from transparent and high pH resistant plastics.

As shown in FIG. 4, the detector cartridge 20 is built in a vertical orientation, having an assembly area for the detection membrane 21 (FIG. 4), whereby the position of this assembly area secures the maximal range of operating angles of the explosive detector, wherein the membrane 21 is fully submerged under the level of detection liquid. The fully submerged membrane 21 (FIG. 4) represents a fundamental condition for the proper operation of the whole detection system and its detection stability.

As also shown in FIG. 4, the detector cartridge 20 is closed with on optical sensing window 25, located between the submerged site of the molecular membrane 21 and the sensing cap 23 to minimize the length of the optical path for transferring the generated photons to the single photon detection unit 3 (FIG. 4).

As shown in FIG. 4, the detection cartridge is equipped with four triangular leading rails 26 for inserting the sensing cap 23. The cap support 27 is arranged for a sealed positioning of the sensing cap 23 and the covering black rear rectangular lid 28 together with optical shield 29.

The sensing cap 23 is attached using the leading rails 26 of the detector cartridge 20, providing thus the connection between the thermal decomposition unit 2 (FIG. 2) and the detection membrane 21 (FIG. 4) by means of the input/output openings 30 and also the reaction annular chamber 22 (FIG. 4), providing a proper volume for an adequate gas lavation around the dry surface of the molecular membrane.

The sensing cap 23 (FIG. 4) is manufactured from the flexible plastics, securing the adequate gas and liquid sealing of the sensing cap 23 along its cap support 27 (FIG. 4), and being chemically resistant against the measured media and/or the detection liquid.

The sensing cap 23 contains two input/output openings 30 for connecting a gas input/output connection needles 31 (FIG. 3).

The single photon detection unit 3 (FIG. 4) consists of an especially developed photomultiplier lamp 32, sensing analogue electronics, a high voltage source and a control processor, that controls the operation of the single photon detection unit 3 and provides the first level of the digital signal processing, converting the photomultiplier analogue signal to the digital stream, with digital noise reduction and automatic baseline handling.

The digital output of the single photon detection unit 3 (FIG. 4) is further processed by a system computer located at a main processor and an interface board 33, which comprises a power board, a charging board and a communication board 34 (FIG. 3), with an output displayed at a color screen 35 (FIG. 3) either in numerical and graphic form and the output stored on a main system flash disk 36 for example. The main processor and interface board 33 is connected to a power unit 37 and a battery pack 38 (connected by high current battery connectors 39) supplying the whole electronic system. The operating of the system is manually controlled by operator by pressing a control button 40 (FIG. 3) located at the upper part of the explosive detector. The whole constellation of above-described electronic boards are located inside the unit by fixing along a main instrument plastic frame 41. (FIG. 3)

Calibration of the Analytical System

The detection and analytical system according to the invention is calibrated using a calibration device in lieu of certified standards by exposing the detection and analytical system to the known concentration of the known explosives, such as through well characterized solid particles. The calibration device works using the principle of computer controlled continuous thermal vapor phase generator, creating defined flow of defined concentration of the explosive sample in defined number of consequent steps of concentrations, covering thus the whole dynamic range of the detection and analytical system. Multiple thermal vapor phase generators are consequently used to cover the whole wide spectrum calibration for all the existing explosive materials, while each of the generators is used principally just and only for one explosive compound to avoid cross-contamination of the individual thermal vapor phase generator. The calibration system is automatically controlled together with actual device being calibrated by the external computer. The whole calibration procedure is completely robotized, including automatic saving of the calibration results onto the system flash disk for example.

The invention claimed is:

1. Explosives detector configured to perform sampling, thermal decomposition and detection, the explosives detector comprising
   a) an infrared sampler having a flat infrared radiation source suitable for release of a solid explosive sample from a surface of a scanned subject using a wavelength of an infrared radiation,
   b) a thermal decomposition unit having a silica glass tube with a silica glass tube gas inlet located in the flat infrared radiation source, wherein the silica glass tube is equipped with a heating element, the thermal decomposition unit being suitable for decomposing the solid explosive sample into a plurality of explosive molecular fragments, c) a detector cartridge, having a cartridge body with a detection liquid inside, a molecular detection membrane fully submerged under a level of the detection liquid, and a sensing cap, where each explosive molecular fragment is detected by said detector cartridge, d) a single photon optical detection unit in communication with the detector cartridge to provide a data stream indicative of explosive molecular fragment's presence in the solid explosive sample.

2. The explosives detector according to claim 1, wherein the infrared sampler having the flat infrared radiation source is configured to emit infrared energy of infrared wavelength homogeneously to the scanned subject, said flat infrared radiation source being created by a helix-shaped infrared radiation element, said helix-shaped infrared radiation element being covered by a shield dismissing the infrared radiation, said shield having an aperture for the sampling in a direction to the silica glass tube gas inlet.

3. The explosives detector according to claim 1, wherein the thermal decomposition unit has the silica glass tube gas inlet located in the center of the flat infrared radiation source, wherein the heating element of the silica glass tube is a non-linear heating element located at a silica glass tube outer surface in a middle of the silica glass tube length, said heating element including a heating wire wound with non-linear spacing around the silica glass tube to compensate temperature losses at both ends of the silica glass tube and for securing gradient-less distribution of the temperature along the length of the silica glass tube.

4. The explosives detector according to claim 1, wherein the cartridge body comprises a transparent and pH resistant plastic, having a cylindrical cap support and a rim, created as an extension of the said cap support for the molecular detection membrane, said cartridge body having also an optical sensing window, said sensing cap is attached on a cylindrical detection cap support of the detector cartridge, and said sensing cap comprising an inlet for a gas input and an outlet for a gas output for connecting to a gas connection needle installation, said sensing cap having an annular reaction chamber for the explosive molecular fragments circulating around a dry surface of the molecular detection membrane.

5. The explosives detector according to claim 1, wherein the single photon optical detection unit includes a photomultiplier lamp, sensing analogue electronics, a high voltage source and a control processor.

6. The explosives detector according to claim 1, wherein the explosive detector further comprises stored calibration data for a quantitative and a qualitative analysis of the solid explosive sample.

7. A method for detecting explosives, comprising a sampling, a thermal decomposition, a molecular detection and an analysing of a solid explosive sample, characterised in that the method comprises the following operational steps:

a) a releasing of the solid explosive sample using an infrared sampler having a flat infrared radiation source utilising a wavelength of an infrared radiation, b) a thermal decomposition of the explosive sample into a plurality of explosive molecular fragments for obtaining a gas sample thereof, wherein the thermal decomposition is performed in a thermal decomposition unit having a silica glass tube with a silica glass tube gas inlet located in the flat infrared radiation source, and wherein the silica glass tube is equipped with a heating element, c) a molecular detection, in which a detection cartridge has a molecular detection membrane fully sunk under a level of a detection liquid, wherein the molecular detection is performed in a detector cartridge, having a cartridge body with a detection liquid inside, a molecular detection membrane fully submerged under a level of the detection liquid, and a sensing cap, wherein each explosive molecular fragment is detected by said detector cartridge, d) converting a decomposed explosive molecular fragment's concentration to an optical signal, e) analysing the optical signal and determining the content of the explosive sample.

\* \* \* \* \*